(12) United States Patent
Yanagisawa et al.

(10) Patent No.: US 8,664,373 B2
(45) Date of Patent: Mar. 4, 2014

(54) METHOD FOR PRODUCING SOPHOROSE LIPID

(75) Inventors: Satohiro Yanagisawa, Hyogo (JP);
Shigeru Kawano, Hyogo (JP);
Yoshihiko Yasohara, Hyogo (JP)

(73) Assignee: Kaneka Corporation, Osaka (JP)

( * ) Notice: Subject to any disclaimer, the term of this patent is extended or adjusted under 35 U.S.C. 154(b) by 139 days.

(21) Appl. No.: 13/126,532

(22) PCT Filed: Oct. 23, 2009

(86) PCT No.: PCT/JP2009/068260
§ 371 (c)(1),
(2), (4) Date: Jun. 14, 2011

(87) PCT Pub. No.: WO2010/050413
PCT Pub. Date: May 6, 2010

(65) Prior Publication Data
US 2011/0237531 A1 Sep. 29, 2011

(30) Foreign Application Priority Data

Oct. 28, 2008 (JP) .................................. 2008-276201

(51) Int. Cl.
*C07H 15/04* (2006.01)
*C07H 15/10* (2006.01)

(52) U.S. Cl.
CPC ................ *C07H 15/04* (2013.01); *C07H 15/10* (2013.01)
USPC ....................................................... 536/18.2

(58) Field of Classification Search
None
See application file for complete search history.

(56) References Cited

U.S. PATENT DOCUMENTS

| 5,520,839 A | 5/1996 | Hall et al. | |
|---|---|---|---|
| 5,900,366 A * | 5/1999 | Marchal et al. | 435/123 |
| 6,433,152 B1 * | 8/2002 | Lang et al. | 536/18.5 |
| 2005/0164955 A1 | 7/2005 | Gross et al. | |

FOREIGN PATENT DOCUMENTS

| JP | 54-028895 | 3/1979 |
|---|---|---|
| JP | 2001-522597 | 11/2001 |
| WO | 2004/044216 A1 | 5/2004 |
| WO | 2006/069175 A2 | 6/2006 |

OTHER PUBLICATIONS

McCaffrey et al., "Sophorolipids Production by *Candida bombicola* Using Self-Cycling Fermentation" (Journal of Fermentatio nand Bioengineering Journal of Fermentation and Bioengineering (1995) vol. 79 No. 2 pp. 146-151.*

Hu, et al. Purification of lactonic sophorolipids by crystallization, Journal of Biotechnology May 18, 2001 Elsevier NL, vol. 87, No. 3, 2001, pp. 263-272.
Daniel, et al. Production of sophorolipids from whey: development of a two-stage process with *Cryptococcus curvatus* ATCC 20509 and *Candida bombicola* ATCC 22214 using deproteinized whey concentrates as substrates, Appl. Microbiol. Biotechnol., 1999, vol. 51, No. 1, pp. 40-45.
Daniel, et al. Production of sophorolipids in high concentration from deproteinized whey and rapeseed oil in a two stage fed batch process using *Candida bombicola* ATCC 22214 and *Cryptococcus curvatus* ATCC 20509, Biotechnol. Lett., 1998, vol. 20, No. 12, pp. 1153-1156.
Pekin, et al. Production of Sophorolipids from *Candida bombicola* ATCC 22214 Using Turkish Corn Oil and Honey, Eng. Life Sci., 2005, vol. 5, No. 4, pp. 357-362.
Van Bogaert, I.N.A, et al. Microbial production and application of sophorolipids, Appl. Microbiol. Biotechnol., 2007, vol. 76, No. 1, pp. 23-34.
Casas, et al. Sophorolipid Production by *Candida bombicola*: Medium Composition and Culture Methods, J. Biosci. Bioeng., 1999, vol. 88, No. 5, pp. 488-494.
Casas, et al. Optimization of synthetic medium for *Candida bombicola* growth using factorial design of experiments, Enzyme Microb. Technol., 1997, vol. 21, No. 3, pp. 221-229.
McCaffrey, et al. Sophorolipids Production by *Candida bombicola* Using Self-Cycling Fermentation, J. Ferment. Bioeng., 1995, vol. 79, No. 2, pp. 146-151.
Cavalero, et al. The effect of medium composition on the structure and physical state of sophorolipids produced by *Candida bombicola* ATCC 22214, J. Biotechnol., 2003, vol. 103, No. 1, pp. 31-41.
Shah, et al. Sophorolipids Microbial Glycolipids with Anti-Human Immunodeficiency Virus and Sperm-Immobilizing Activities, Antimicrob. Agents Chemother., 2005, vol. 49, No. 10, pp. 4093-4100.
Glenns, et al. Effect of Substrate on Sophorolipid Properties, J. Am. Oil Chem. Soc., 2006, vol. 83, No. 2 pp. 137-145.
Asmer, et al. Microbial Production, Structure Elucidation and Bioconversion of Sophorose Lipids, Journal of the American Oil Chemists' Society, vol. 65, No. 9, 1988, pp. 1460-1466.
Davila, et al. Sophorose lipid production from lipidic precursors: predictive evaluation of industrial substrates, Journal of Industrial Microbiology, vol. 13, 1994, pp. 249-257.
Gorin, et al. Hydroxy Fatty Acid Glycosides of Sophorose from *Torulopsis magnoliae*, Canadian Journal of Chemistry, vol. 39, 1961, pp. 846-855.
Lang, et al. Antimicrobial Effects of Biosurfactants, Fett Wissenschaft Technologie, vol. 91, 1989, pp. 363-366.
International Search Report for International Application No. PCT/JP2009/068260 mailed on Feb. 2, 2010.
International Preliminary Report on Patentatbility for Application No. PCT/JP2009/068260 issued on Jun. 7, 2011.

* cited by examiner

Primary Examiner — Eric S Olson
(74) Attorney, Agent, or Firm — Turocy & Watson, LLP (57) ABSTRACT

The present invention provides a low-cost, efficient method for producing a glycolipid biosurfactant, in particular, lactonic sophorose lipids. This method is characterized by culturing a microorganism capable of producing the biosurfactant under limited oxygen supply. The present invention enables preferential production of lactonic sophorose lipids and facilitates recovery of the lactonic sophorose lipids in a solid form. Further, the present invention enables production of high purity acidic sophorose lipids by hydrolyzing high purity lactonic sophorose lipids produced by the above method. The present invention also provides lactonic sophorose lipids that possess strong antibacterial and antifungal activities, and an antibacterial and/or antifungal agent containing the sophorose lipids.

6 Claims, 1 Drawing Sheet

METHOD FOR PRODUCING SOPHOROSE LIPID

TECHNICAL FIELD

The present invention relates to sophorose lipids and a method for producing sophorose lipids, and also relates to an antibacterial and/or antifungal agent containing sophorose lipids as active ingredients.

BACKGROUND ART

Biosurfactants are surface active agents produced by microorganisms and are known to possess various bioactivities as well as surface activity. Since biosurfactants exhibit a high degree of biodegradability and are low toxic and hypoallergenic to animals and plants, these environmentally and human friendly compounds are expected to be applied in various fields. There have been known some biosurfactants such as glycolipid biosurfactants, peptide biosurfactants, and fatty acid biosurfactants.

Sophorose lipids are a type of glycolipid biosurfactants and have a structure in which sophorose consisting of two glucose molecules is linked to a fatty acid by a glycosidic ether bond. Sophorose lipids are categorized into two forms: the lactone form in which the carboxyl group in the fatty acid side chain and the sophorose moiety form a cyclic ester bond; and the acid form in which the bond is hydrolyzed. In addition to these forms, there exists a number of derivatives which are characterized by the presence or absence of double bonds in the fatty acid side chain, the length of the carbon chain, the position of the glycosidic ether bond, the presence or absence of acetyl groups introduced to the hydroxyl groups of the sugar moiety, and other structural parameters (Non-Patent Document 1). Cultivation of yeast cells on a culture substrate including a sugar and/or an oil or fat provides a mixture of these forms of sophorose lipid, and the composition of the mixture depends on the used culture substrate (Non-Patent Document 2). The composition of the fatty acid side chains of the sophorose lipids also depends on the type of culture substrate used (Non-Patent Document 2).

As known in the art, sophorose lipids are generally produced in a highly viscous oil form that is difficult to handle (Non-Patent Document 3). For example, a sophorose lipid oil obtained from a liquid culture by inclined sedimentation is an oil with a water content of 40 to 50%. Then, sophorose lipids are extracted from this oil with an organic solvent in order to increase the purity, and the obtained sophorose lipids have a remarkably high viscosity (Patent Document 1).

The use of a culture substrate including an alkane such as hexadecane results in the production of sophorose lipids mainly composed in particular of the diacetyl lactone form among the lactone forms. The diacetyl lactone form is known to have comparatively high hydrophobicity and crystallize out of the liquid culture (Non-Patent Document 4). This method is useful because sophorose lipids are produced in an easy-to-handle solid form. However, industrial application of this method is impractical because alkanes to be used are expensive materials.

Many studies on the production of sophorose lipids using an inexpensive material such as a vegetable oil or fat, or a fatty acid derived from a vegetable oil or fat have been reported. However, all of them demonstrate the production of sophorose lipids in an oil form, not in a solid form, except only one that demonstrates the production of sophorose lipids in a solid form from a liquid culture obtained by using a culture substrate including Turkish corn oil (Non-Patent Document 5). Non-Patent Document 5, however, teaches that sophorose lipids may be produced in a viscous honey form depending on the culture method. In other words, Non-Patent Document 5 fails to provide sufficient knowledge of the culture conditions for producing solid sophorose lipids. In addition, Non-Patent Document 5 does not teach any composition ratio of the produced solid sophorose lipids (e.g. the ratio of the lactonic form and the acid form, the ratio of the diacetyl lactone form, the monoacetyl lactone form and the diol lactone form, and the ratio of saturated fatty acid side chains to unsaturated fatty acid side chains in all fatty acid chains).

There are also many studies on improvement of the productivity of sophorose lipids. It is known that a key to increase the production of sophorose lipids is to culture microorganism cells in aerobic conditions (Non-Patent Document 6). One measure to achieve this culture conditions is, for example, to increase the stirrer speed to maintain a high dissolved oxygen saturation level when the dissolved oxygen saturation level decreases with proliferation of the microorganism cells (Non-Patent Document 5). All of these studies also do not teach any relationship between culture conditions (e.g. aeration conditions) and the composition ratio of produced sophorose lipids (e.g. the ratio of the lactone form and the acid form, the ratio of the diacetyl lactone form, the monoacetyl lactone form and the diol lactone form, and the ratio of saturated fatty acid side chains to unsaturated fatty acid side chains in all fatty acid chains).

Lactonic sophorose lipids possess stronger antibacterial activities compared to acidic sophorose lipids, and in particular, sophorose lipids in the diacetyl form or the monoacetyl form are known to possess further stronger activities (Non-Patent Document 7). In addition, lactonic sophorose lipids, for example, obtained from a liquid culture obtained by using a culture medium including oleic acid have been reported to possess antibacterial and antifungal activities (Patent Documents 2 and 3 and Non-Patent Document 7). All of these reports, however, do not teach any relationship between the structure of the fatty acid side chain of the sophorose lipid and its antibacterial activity.

Acidic sophorose lipids are highly water soluble. In the case that acidic sophorose lipids are produced in a liquid culture, isolation thereof from the culture is difficult. Only purification by chromatography is known to do this (Non-Patent Document 1), but it is substantially impractical for industrial applications. A method for producing acidic sophorose lipids by hydrolyzing lactonic sophorose lipids is also known (Patent Document 1). However, at present, it is remarkably difficult to obtain high purity acidic sophorose lipids at low cost because, in the first place, there is no known method for obtaining high purity lactonic sophorose lipids at low cost.

Patent Document 1: JP-A S54-28895
Patent Document 2: WO 2004/044216
Patent Document 3: WO 2006/069175
Non-Patent Document 1: Journal of the American Oil Chemists' Society, vol. 65, no. 9, 1460 (1988)
Non-Patent Document 2: Journal of Industrial Microbiology, vol. 13, 249 (1994)
Non-Patent Document 3: Canadian Journal of Chemistry, vol. 39, 846 (1961)
Non-Patent Document 4: Journal of the American Oil Chemists' Society, vol. 83, no. 2, 137 (2006)
Non-Patent Document 5: Engineering in Life Sciences, vol. 5, no. 4, 357 (2005)
Non-Patent Document 6: Applied Microbiology and Biotechnology, vol. 76, 23 (2007)

Non-Patent Document 7: Fett Wissenschaft Technologie, vol. 91, 363 (1989)

SUMMARY OF THE INVENTION

An object of the present invention is to provide a method for producing from an inexpensive oil or fat, a glycolipid biosurfactant having a specific structure, in particular, sophorose lipids with a high mole percent of the diacetyl lactone form. Another object of the present invention is to provide sophorose lipids with a high mole percent of the diacetyl lactone form, in particular, in an easy-to-handle solid form. Still another object of the present invention is to provide an antibacterial and/or antifungal agent containing, as active ingredients, sophorose lipids with a high mole percent of the diacetyl lactone form and, in particular, a high degree of saturation of the fatty acid side chains. Still another object of the present invention is to provide high purity acidic sophorose lipids and a method for producing the high purity acidic sophorose lipids at low cost.

In order to overcome the above problems, the present inventors studied conditions for increasing the production of lactonic sophorose lipids having strong antibacterial and antifungal activities from an inexpensive oil or fat. The study revealed that the mole percent of the diacetyl lactone form is increased by culturing a microorganism capable of producing a biosurfactant under limited oxygen supply to a liquid culture. The study also revealed that sophorose lipids can be easily produced in an easy-to-handle solid form in the case that the mole percent of the diacetyl lactone form is at least 80% or higher, and that high purity acidic sophorose lipids can be easily produced by using the obtained high purity lactonic sophorose lipids as a raw material. Furthermore, the study revealed that among these sophorose lipids rich in the lactone form, lactonic sophorose lipids having a saturated fatty acid side chain possess remarkably strong antibacterial and antifungal activities. With these findings, the present inventors completed the present invention.

One aspect of the present invention is a method for producing a glycolipid biosurfactant, including culturing a microorganism under limited oxygen supply.

Another aspect of the present invention is the above production method wherein oxygen supply is controlled such that a dissolved oxygen saturation level is 20% or lower during the culturing except an initial stage.

A still another aspect of the present invention is the above production method wherein the glycolipid biosurfactant is sophorose lipids.

A still another aspect of the present invention is the above production method wherein the sophorose lipids have a mole percent of diacetyl lactonic sophorose lipids of not lower than 80% based on the total moles of lactonic sophorose lipids.

A still another aspect of the present invention is the above production method wherein the glycolipid biosurfactant has a mole percent of saturated fatty acid residues of not lower than 40% based on the total moles of fatty acid residues constituting fatty acid side chains.

A still another aspect of the present invention is the above production method wherein the sophorose lipids have a mole percent of saturated fatty acid residues of not lower than 40% based on the total moles of fatty acid residues constituting fatty acid side chains.

A still another aspect of the present invention is the above production method wherein an oil or fat is used as a raw material.

A still another aspect of the present invention is the above production method wherein the microorganism is *Candida bombicola*.

A still another aspect of the present invention is the above production method further including crystallizing the glycolipid biosurfactant.

A still another aspect of the present invention is the above production method wherein the glycolipid biosurfactant is produced in a solid form.

A still another aspect of the present invention is the above production method further including hydrolyzing a lactone form of the glycolipid biosurfactant into an acid form.

A still another aspect of the present invention is sophorose lipids having a mole percent of saturated fatty acid residues of not lower than 40% based on the total moles of fatty acid residues constituting fatty acid side chains.

A still another aspect of the present invention is sophorose lipids having a mole percent of diacetyl lactonic sophorose lipids of not lower than 80% based on the total moles of lactonic sophorose lipids.

A still another aspect of the present invention is sophorose lipids having a mole percent of saturated fatty acid residues of not lower than 40% based on the total moles of fatty acid residues constituting fatty acid side chains.

A still another aspect of the present invention is sophorose lipids having a mole percent of diacetyl lactonic sophorose lipids of not lower than 80% based on the total moles of lactonic sophorose lipids.

A still another aspect of the present invention is sophorose lipids which are in a solid form.

A still another aspect of the present invention is a composition containing a glycolipid biosurfactant produced by the above production method and/or the above sophorose lipids.

A still another aspect of the present invention is a surface active agent containing the above composition.

A still another aspect of the present invention is use of the above surface active agent in a food product application, household product application, daily commodity application, civil engineering and building material application, paint and ink application, rubber and plastic application, machine and tool application, medical and cosmetic application, livestock and fishery application or agriculture application, or during the manufacture of a product.

A still another aspect of the present invention is an antibacterial and/or antifungal agent containing the above composition.

A still another aspect of the present invention is use of the above antibacterial and/or antifungal agent in a food product application, household product application, daily commodity application, construction and paint application, machine and tool application, water treatment application, separation application, medical and cosmetic application, livestock and fishery application, or agriculture application.

A still another aspect of the present invention is a medicament containing the above composition.

A still another aspect of the present invention is a method for producing acidic sophorose lipids, including hydrolyzing the above sophorose lipids.

The present invention enables the production of a glycolipid biosurfactant having a specific structure, in particular, sophorose lipids with a high mole percent of the diacetyl lactone form, from an inexpensive oil or fat. The present invention also enables the production of sophorose lipids with a high mole percent of the diacetyl lactone form, in particular, in a solid form. Further, the present invention provides sophorose lipids with a high mole percent of the diacetyl lactone form and, in particular, a high degree of saturation of the fatty acid side chains. These sophorose lipids are useful as an antibacterial and/or antifungal agent because they possess remarkably high antibacterial and antifungal activities. The present invention further provides high purity acidic sophorose lipids by hydrolyzing high purity lactonic sophorose lipids with an acid or alkali, and a method for producing the high purity acidic sophorose lipids at low cost.

BEST MODE FOR CARRYING OUT THE INVENTION

Hereinafter, the present invention is described in more detail based on embodiments.

1. Glycolipid Biosurfactant

Glycolipid biosurfactants are surface active agents produced by microorganisms and contain a sugar moiety serving as a hydrophilic group and a hydrocarbon chain serving as a hydrophobic group. Examples thereof include sophorose lipids, mannosylerythritol lipids, rhamnose lipids, and trehalose lipids.

2. Sophorose Lipid

Sophorose lipids are a type of glycolipid biosurfactants and are generally categorized into two forms: the lactone form represented by the following formula (1):

[Formula 1]

wherein $R_1$ and $R_2$ each represent H or $COCH_3$; $R_3$ represents H or $CH_3$; and $R_4$ represents a saturated or unsaturated $C_{12-16}$ hydrocarbon group when $R_3$ is H, and $R_4$ represents a saturated or unsaturated $C_{11-15}$ hydrocarbon group when $R_3$ is $CH_3$, and the acid form represented by the following formula (2)

[Formula 2]

wherein $R_1$ to $R_4$ are as defined above.

As is clear from the above, sophorose lipids have a number of derivatives which are characterized by the positions and number of acetyl groups, the presence or absence of double bonds in the fatty acid side chain, the length of the carbon chain of the fatty acid side chain, the position of the glycosidic ether bond in the fatty acid side chain, the positions of hydroxyl groups on the sophorose moiety that is a part of a lactone ring, and other structural parameters. Sophorose lipids generally occur as a mixture of these compounds. In general, sophorose lipids are produced in a highly viscous oil form that is difficult to handle. However, sophorose lipids in the diacetyl lactone form, which are comparatively high in hydrophobicity, can be produced in a solid form.

3. Microorganism

The glycolipid biosurfactant according to the present invention can be produced by culturing a microorganism capable of producing a glycolipid biosurfactant. Any microorganism capable of producing a glycolipid biosurfactant can be used. For example, for the production of sophorose lipids, yeasts of the genera *Candida, Torulopsis, Wickerhamiella*, and *Starmerella* are preferable. In particular, yeasts of the genus *Candida* are preferable, and *Candida bombicola, Torulopsis apicola*, and the like are more preferable. *Candida bombicola* ATCC 22214 is most preferable.

4. Culture Medium

The glycolipid biosurfactant, for example, sophorose lipids, can be produced by culturing the above-mentioned microorganism in a culture medium described below.

For the culture process in the present invention, any medium can generally be used, provided that it contains assimilable nutritional sources for yeast cells. For example, usable are common media appropriately containing materials mixed therein. Examples of the materials include carbon sources such as sugars (e.g. glucose, sucrose, maltose), organic acids (e.g. lactic acid, acetic acid, citric acid, propionic acid), alcohols (e.g. ethanol, glycerin), hydrocarbons (e.g. paraffin), oils and fats (e.g. soybean oil, rapeseed oil), and mixtures of these; nitrogen sources such as ammonium sulfate, ammonium phosphate, urea, yeast extracts, meat extracts, peptone, and corn steep liquor; and other nutritional sources such as mineral salts and vitamins.

A sugar and/or an oil or fat may be used as a main raw material. Glucose is the preferred sugar as a main raw material. Examples of oils and fats as a main raw material include animal and vegetable oils and fats. Examples of vegetable oils and fats include rapeseed oil, soybean oil, sunflower oil, coconut oil, cottonseed oil, corn oil, palm oil, palm kernel oil, flaxseed oil, and castor oil. Unsaturated fatty acids, saturated fatty acids, unsaturated fatty acid esters, saturated fatty acid esters, and the like produced from these vegetable oils and fats may be used. Among these, saturated fatty acid esters are preferable, and saturated fatty acid esters having a $C_{16-48}$ acyl group are suitably used. These fatty acid esters are not particularly limited with respect to the ester species and may be any ester species such as methyl esters, ethyl esters, propyl esters, isopropyl esters, and butyl esters. Methyl esters and ethyl esters are preferable, and methyl esters are more preferable. Most preferable oils and fats are palm oil, methyl palmitate, methyl stearate, and mixtures of these.

5. Culture Conditions

In the present invention, the culture pH, culture temperature, and culture period may be set to common conditions. Preferably, for example, the pH is set to 2.5 to 9.5, the temperature is set to 20° C. to 45° C., and the period is set to 4 to 14 days.

The mole percent of the diacetyl lactone form of sophorose lipid is increased by controlling oxygen supply to a liquid culture to a level lower than common aerobic culture conditions. The mole percent of the diacetyl lactone form is described later. The oxygen supply can be controlled by the aeration amount and/or stirring conditions. Generally, the oxygen supply can be limited by, for example, reducing the aeration amount, reducing the stirrer speed, or changing the culture apparatus. This leads to suppression of foaming of the liquid culture caused by the biosurfactant accumulated with time of culture.

For example, since the dissolved oxygen saturation level starting from 100% immediately after culture initiation remarkably decreases due to oxygen consumption in the liquid culture along with proliferation of microbial cells, measures to maintain a high dissolved oxygen saturation level, such as increasing the aeration amount, or stirrer speed, are generally used in a common aerobic culture process. In the present invention, on the other hand, the oxygen supply is controlled such that the dissolved oxygen saturation level is kept low during the culture process. For example, the oxygen supply is controlled during the culture process, except an initial culture stage immediately after culture initiation in which microbial cells proliferate, such that the dissolved oxygen saturation level is 20% or lower, preferably 15% or lower, more preferably 10% or lower, further more preferably 5% or lower, and most preferably 0%. Although the dissolved oxygen saturation level is temporarily increased for several hours to half day by changing the aeration condition, the below-mentioned mole percent of the diacetyl lactone form is not largely affected and therefore such increase does not cause any problem. The "initial culture stage immediately after culture initiation in which microbial cells proliferate" means a period of 0 to 3 days, preferably 0 to 2 days, and most preferably 0 to 1 day after culture initiation. During the initial culture stage immediately after culture initiation, it is only necessary to supply the amount of oxygen needed for proliferation of microbial cells. The dissolved oxygen saturation level is not required to start from 100%. For example, in the case of using a common 5 L mini jar fermenter at a stirrer speed of 450 rpm, the aeration condition is preferably 0.4 vvm or less, more preferably 0.2 vvm or less, and most preferably 0.1 vvm or less. For example, for shaking culture in a 500 ml shaking (Sakaguchi) flask, the amount of the culture medium is preferably not less than 100 ml. Since the accumulating rate of sophorose lipids is enhanced by increasing the aeration amount during the culture process, the oxygen supply may be increased within the above range.

6. Composition of Sophorose Lipids

The composition of sophorose lipids produced by fermentation can be determined by an analysis under the identical or equivalent HPLC conditions to those taught in J. Chromatogr., vol. 648, 139 (1993). The elution patterns of various sophorose lipids of different structures under these analysis conditions are described in the document. By comparing this data and elution patterns actually obtained by the analysis, compounds corresponding to respective elution peaks can be identified.

Sophorose lipids obtained by the culture process in the present invention are mainly composed of lactonic sophorose lipids and include a low mole percent of acidic sophorose lipids.

The lactonic sophorose lipids may be composed of the diacetyl lactone form (in the formula (1), both of $R_1$ and $R_2$ are $COCH_3$), the monoacetyl lactone form (in the formula (1), either $R_1$ or $R_2$ is $COCH_3$ and the other is H), and the diol lactone form (in the formula (1), both of $R_1$ and $R_2$ are H). The molar ratio of these forms varies depending on the amount of supplied oxygen among the above culture conditions. Solid sophorose lipids produced by the later-described method for producing solid sophorose lipids are mainly composed of the diacetyl lactone form. Since sophorose lipids with a mole percent of the diacetyl lactone form of less than 80% are less likely to crystallize out as a solid, the mole percent of the diacetyl lactone form is preferably higher. Here, the term "mole percent of the diacetyl lactone form" means a proportion of the diacetyl lactone form in lactonic sophorose lipids composed of the diacetyl lactone form, monoacetyl lactone form, and diol lactone form. Since, as described later, the diacetyl lactone form exhibits strong antibacterial activity, the mole percent of the diacetyl lactone form is preferably higher in the case that produced sophorose lipids are intended for use as an antibacterial and/or antifungal agent. Accordingly, the mole percent of the diacetyl lactone form based on the total moles of sophorose lipids produced by fermentation is preferably not lower than 80%, more preferably not lower than 85%, further more preferably not lower than 90%, and most preferably not lower than 95%.

The fatty acid side chains of the sophorose lipids may be all saturated or unsaturated, or alternatively some of them may be saturated and the others may be unsaturated. The mole percent of saturated and unsaturated fatty acid side chains can be controlled by selecting an oil or fat used in the culture process. In order to produce sophorose lipids rich in saturated fatty acid side chains, an oil or fat rich in saturated fatty acids may be used, and in order to produce sophorose lipids rich in unsaturated fatty acid side chains, an oil or fat rich in unsaturated fatty acids may be used. As described later, among sophorose lipids in the diacetyl lactone form, those having a saturated fatty acid side chain possess particularly strong antibacterial and antifungal activities. Therefore, the mole percent of saturated fatty acid side chains based on the total moles of fatty acid side chains is preferably higher in the case that the sophorose lipids are intended for use as an antibacterial and/or antifungal agent. Specifically, the mole percent of saturated fatty acid side chains based on the total moles of fatty acid side chains is preferably not lower than 40%, more preferably not lower than 60%, further more preferably not lower than 80%, and most preferably not lower than 90%.

7. Recovery of Sophorose Lipids

The sophorose lipids of the present invention can be recovered as follows.

The liquid culture is left to allow almost the entire sophorose lipids produced to quickly precipitate to the bottom of the culture. Thus, the sophorose lipids can be obtained in high yield by collecting the precipitates. In this case, the yield can be increased by heating the culture to about 80° C. because the flowability of the sophorose lipids is improved and the sophorose lipids are more likely to be easily separated. In order to remove impurities from the obtained sophorose lipids, the sophorose lipids may be rinsed with water, an aqueous buffer, an organic solvent such as hexane, or the like.

From the sophorose lipids thus obtained, solid sophorose lipids can be obtained by a purification method that increases the purity of the diacetyl lactone form. For example, the method is as follows. Fat-soluble impurities such as unused oil and fat can be removed by rinsing the sophorose lipids produced by the above method, with an organic solvent such as hexane. Water and water-soluble impurities can be removed by extracting the sophorose lipids with an organic solvent such as ethyl acetate or toluene. These processes for removing impurities may be performed or may not be performed. The organic solvent used for extraction can be easily distilled off by vacuum concentration. In order to isolate sophorose lipids in a solid form from the sophorose lipids thus obtained, a solvent capable of crystallizing sophorose lipids, such as water or an aqueous buffer, may be used to crystallize sophorose lipids therefrom. For crystallization from water, an aqueous buffer or the like, the pH is preferably neutral to acidic, and particularly preferably around neutral. Specifically, the pH is 1 to 8, preferably 2 to 7.5, more preferably 3 to 7, and most preferably 6 to 7. Sophorose lipids are crystallized out by stirring the mixture after adjusting the pH. The crystallization is preferably performed at low temperature because the yield is increased. Preferably, the liquid to be crystallized is cooled to a temperature at which the liquid does not freeze, for example about 4° C., under stirring to grow crystals. Isolation of solid sophorose lipids from this liquid can be achieved by a common method such as centrifugation or filtration. The purification method by crystallization is suitably used for the production of sophorose lipids according to the present invention, in particular, for the production of sophorose lipids with a high mole percent of the diacetyl lactone form, and of sophorose lipids with a high mole percent of saturated fatty acid side chains, as well. The purification method by crystallization is also suitably used for the production of biosurfactants other than sophorose lipids, provided that they are glycolipid biosurfactants produced by the present invention.

8. Antibacterial and Antifungal Activities and Composition of Fatty Acid Side Chains The term "antibacterial and antifungal activities" in the context of the present invention means an effect of inhibiting proliferation of microorganisms such as bacteria, yeasts, and molds, that is, an effect of reducing or killing viable cells of these microorganisms.

Among lactonic sophorose lipids that are known to possess antibacterial and antifungal activities, those which have a mole percent of saturated fatty acid side chains based on the total moles of fatty acid side chains is not lower than 40%, preferably not lower than 60%, more preferably not lower than 80%, and further more preferably not lower than 90% possess strong antibacterial and antifungal activities. These sophorose lipids are preferably used as an antibacterial and/or antifungal agent. In the case that these are used as an antibacterial and/or antifungal agent, the amount of the agent to be used may be suppressed because these exhibit the effect even at a lower concentration, compared to conventional antibacterial and/or antifungal agents.

The target microorganism of the antibacterial and/or antifungal agent of the present invention is not particularly limited. The antibacterial and/or antifungal agent of the present invention is effective against, for example, gram-positive bacteria. Examples of gram-positive bacteria include bacteria of the following genera: *Micrococcus, Stomatococcus, Planococcus, Staphylococcus, Deinococcus, Streptococcus, Leuconostoc, Pediococcus, Aerococcus, Gemella, Peptococcus, Peptostreptococcus, Ruminococcus, Coprococcus, Sarcina, Bacillus, Sporolactobacillus, Clostridium, Desulfotomaculum, Sporosarcina, Oscillospira, Lactobacillus, Listeria, Erysipelothrix, Brochothrix, Renibacterium, Kurthia, Caryophanon, Corynebacterium, Gardenerella, Arcanobacterium, Arthrobacter, Brevibacterium, Curtobacterium, Caseobacter, Microbacterium, Aureobacterium, Cellulomonas, Agromyces, Arachnia, Rothia, Propionibacterium, Eubacterium, Acetobacterium, Lachnospira, Butyrivibrio, Thermoanaerobacter, Actinomyces, Bifidobacterium, Mycobacterium, Nocardia, Rhodococcus, Nocardioides, Pseudonocardia, Oerskovia, Saccharopolyspora, Micropolyspora, Promicromonospora*, and *Intrasporangium*.

The antibacterial and/or antifungal agent of the present invention is suitably used against bacteria of the genera *Bacillus, Staphylococcus*, and *Corynebacterium* among these.

In particular, the antibacterial and/or antifungal agent of the present invention is suitably used against bacteria of the genus *Staphylococcus* (specifically *Staphylococcus aureus* and *Staphylococcus epidermidis*); bacteria of the genus *Corynebacterium* (specifically *Corynebacterium xerosis*); bacteria of the genus *Streptococcus* (specifically *Streptococcus suis* and *Streptococcus bovis*); bacteria of the genus *Propionibacterium* (specifically *Propionibacterium acnes*); and the like.

Examples of yeasts and molds include species of the genera *Cladosporium, Aspergillus, Fusarium, Penicillium, Gloeophyllum, Schizophyllum, Candida, Saccharomyces, Pichia*, and *Rhodotorula*.

In particular, the antibacterial and/or antifungal agent of the present invention is suitably used against species of the genera *Saccharomyces, Cladosporium, Aspergillus, Fusarium, Penicillium, Gloeophyllum*, and *Schizophyllum*, and the like.

9. Application

Since the glycolipid biosurfactant produced in the present invention possesses surface active agent properties, and antibacterial and antifungal activities, it can be used in fields requiring these properties. If a novel property or function is discovered, the glycolipid biosurfactant will extend its application to fields that require such a property or function.

Examples of applications of the glycolipid biosurfactant produced in the present invention as a surface active agent include food product applications (e.g. emulsifiers, antifungal agents); household product applications (e.g. detergents for toilet, bath, kitchen or the like, detergents for washing (softening agents, antistatic agents)); daily commodity applications (e.g. rust inhibitors, disinfectants); civil engineering and building material applications (e.g. concrete admixtures, water reducing agents); paint and ink applications (e.g. water-based ink applications, antifoaming agents, dispersants); rubber and plastic applications (e.g. antistatic agents, antifogging agents, dispersants); machine and tool applications (e.g. disinfectants, detergents, rust inhibitors); medical and cosmetic applications (e.g. medicaments, cosmetics, perfumes, disinfectants); livestock and fishery applications (e.g. feed additives, antibacterial agents); and agriculture applications (e.g. agricultural chemicals, soil conditioners, disinfectants); and applications during the manufacture of a product (fields such as paper and pulp materials, rubber and plastic materials, and fiber materials).

Examples of applications of the glycolipid biosurfactant produced in the present invention as an antibacterial and/or antifungal agent include food product applications (e.g. preservatives, shelf life-extending agents, freshness keeping agents); household product applications (e.g. brush products, stationeries, sundry articles (insoles for shoes, etc.), interior items (furniture, etc.), covering materials for walls, floors, ceilings and the like, equipment and articles for wet areas including toilet, bath and kitchen); daily commodity applications (e.g. textile products, leather products, paper products, rubber products, clothes, packaging materials, packing containers); construction and paint applications (e.g. fixed structures, exterior and interior materials for buildings, wood, metal, concrete and plastic materials); machine and tool applications (e.g. electrical and household electrical devices, machines, vehicles, optical instruments, medical, welfare and sanitary instruments); water treatment applications (e.g. water treatment, waste water treatment, sludge treatment); separation applications (e.g. filtration devices, filtration materials, filtration equipment); medical and cosmetic applications (e.g. medicaments, cosmetics, perfumes); livestock and fishery applications (e.g. feed additives); and agriculture applications (e.g. agricultural chemicals).

The glycolipid biosurfactant produced in the present invention may be used in any form and may be optionally used in combination or admixture with other materials depending on its application. For example, the biosurfactant may be used in a neat form (liquid form or solid form) or may be dissolved in a solvent of any type and used in a liquid form. Alternatively, the biosurfactant may be used in an emulsified form in the presence of water or an organic solvent or may be mixed with a solid material.

The amount of the glycolipid biosurfactant produced in the present invention may be determined depending on the application of the glycolipid biosurfactant. For example, in applications as an antibacterial and/or antifungal agent, the amount of sophorose lipids as active ingredients is not particularly limited and is generally not less than 0.001% by weight, preferably not less than 0.01% by weight, and more preferably not less than 0.1% by weight.

10. Preparation of Acidic Sophorose Lipid

Acidic sophorose lipids can be easily produced with high purity by hydrolyzing high purity solid sophorose lipids produced by the above method as a raw material, with an acid, alkali or the like. For example, sophorose lipids in the diacetyl lactone form are exposed to 3 molar equivalents of sodium hydroxide at room temperature to be immediately hydrolyzed. Thus, a transparent, colorless, high-purity acidic sophorose lipid aqueous solution is obtained. The purity can be further increased by distilling water off from this aqueous solution.

EXAMPLES

Specific examples of the present invention are described below. The present invention, however, is not limited to these examples.

All of the microorganisms used in the examples are available with no restrictions from NITE Biological Resource Center (NBRC), Department of Biotechnology, National Institute of Technology and Evaluation (2-5-8, Kazusakamatari, Kisarazu-shi, Chiba, 292-0818) or American Type Culture Collection (ATCC) in the US.

Example 1

As a seed medium, 50 ml of a liquid medium (0.1% potassium dihydrogen phosphate, 0.5% manganese sulfate heptahydrate, 0.01% iron (II) chloride, 0.01% sodium chloride, 0.4% yeast extract, 10% glucose and 10% rapeseed oil, pH 4.5) was poured into a 500 ml shaking (Sakaguchi) flask. As a main medium, 3 L of a liquid medium (0.1% potassium dihydrogen phosphate, 0.5% manganese sulfate heptahydrate, 0.01% iron (II) chloride, 0.01% sodium chloride, 0.4% yeast extract, 10% glucose and Esterpal-M produced from palm oil (molar ratio (methyl palmitate:methyl stearate)=7:3, Miyoshi Oil & Fat Co., Ltd.), pH 4.5) was poured into a 5 L mini jar fermenter (B.E. MARUBISHI Co., Ltd.). These media were sterilized by steam at 121° C. for 20 minutes. One platinum loop of *Candida bombicola* ATCC 22214 was inoculated to the seed medium and cultured with shaking at 30° C. for one day. The entire seed culture was inoculated to the main medium and cultured at 30° C., 450 rpm and 0.3 vvm for seven days. The dissolved oxygen saturation level reached 0% one day after culture initiation and thereafter stayed at 0%.

The composition of sophorose lipids in the culture was determined by an analysis under the following HPLC conditions.

(HPLC Analysis Conditions)

Column: YMC-Pack Pro C18 RS (150×4.6 mm, 3 μm, YMC Co. Ltd.)

Eluant: linear gradient, 2% acetonitrile aqueous solution→70% acetonitrile aqueous solution (0→48 minutes)

Flow rate: 1.0 ml/min

Column temperature: 30° C.

Detection: Corona charged aerosol detector (ESA, Inc.)

The structure of each sophorose lipid was identified by comparison with the elution times reported in the document (J. Chromatogr., 648, 139 (1993)). Acidic sophorose lipids were eluted after 28 to 34 minutes, sophorose lipids in the monoacetyl lactone form and diol lactone form were eluted after 34 to 45 minutes, and sophorose lipids in the diacetyl lactone form were eluted after 45 to 55 minutes under the above HPLC analysis conditions. The peak area of each form was calculated by integration over the elution time and compared to one another. A molar ratio of the respective peak areas obtained was regarded as the molar ratio of the composition of sophorose lipids. The results revealed that acidic sophorose lipids were not detected at all in the culture after completion of the culture process, that is, the lactone form constituted 100% of the sophorose lipids. The mole percent of the diacetyl lactone form based on the total moles of lactonic sophorose lipids was 81%. The mole percent of saturated fatty acid side chains based on the total moles of fatty acid side chains was 75%.

Example 2

The entire culture obtained in Example 1 was heated to 80° C., whereby an oily substance (about 300 g) was precipitated. The oily substance was rinsed with an equal volume of hexane to remove the unused oil and fat and then extracted with an equivalent volume of ethyl acetate. Thus, an ethyl acetate solution of sophorose lipids was obtained. Ethyl acetate was distilled off by vacuum concentration and then 1.5 L of water was added to the residue. The pH of the resulting mixture was adjusted to 6.5 and the mixture was cooled from room temperature to 4° C. for cooling crystallization. The precipitated crystals were collected by filtration and dried, whereby solid sophorose lipids (18 g) were obtained. The sophorose lipids were analyzed under the HPLC conditions described in Example 1. The results revealed that the mole percent of lactonic sophorose lipids was 100%, that the mole percent of the diacetyl lactone form based on the total moles of lactonic sophorose lipids was 96%, and that the mole percent of saturated fatty acid side chains based on the total moles of fatty acid side chains was 92%.

Example 3

The same culture procedures as described in Example 1 were performed, except that the aeration condition during the main culture was changed to 0.2 vvm. The culture after completion of the culture process was analyzed under the HPLC conditions described in Example 1. The results revealed that acidic sophorose lipids were not detected at all and the mole percent of lactonic sophorose lipids was 100%. The mole percent of the diacetyl lactone form based on the total moles of lactonic sophorose lipids was 89%, and the mole percent of saturated fatty acid side chains based on the total moles of fatty acid side chains was 86%.

Figure 1:
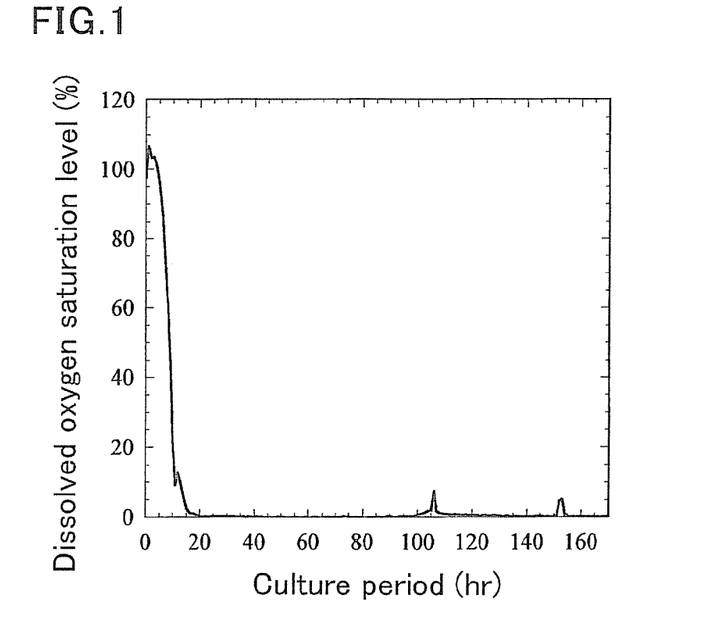
FIG. 1 is a graph showing a temporal change of the dissolved oxygen saturation level under an aeration condition of 0.2 vvm in Example 3 of the present invention.

The temporal change of the dissolved oxygen saturation level during the culture process is illustrated in FIG. 1. The dissolved oxygen saturation level reached 0% one day after culture initiation and thereafter did not rise.

Example 4

The same procedures as described in Example 2 were performed on the culture obtained in Example 3. As a result, an oily substance (about 300 g) was obtained and then crystals were recovered. Thus, solid sophorose lipids (39 g) were obtained. The sophorose lipids were analyzed under the HPLC conditions described in Example 1. The results revealed that the mole percent of lactonic sophorose lipids was 100%, that the mole percent of the diacetyl lactone form based on the total moles of lactic sophorose lipids was 100%, and that the mole percent of saturated fatty acid side chains based on the total moles of fatty acid side chains was 98%.

Reference Example 1

The same culture procedures as described in Example 1 were performed, except that the aeration condition during the main culture was changed to 0.5 vvm. The culture after completion of the culture process was analyzed under the HPLC conditions described in Example 1. The results revealed that the mole percent of lactonic sophorose lipids in the culture was 99%. The mole percent of the diacetyl lactone form based on the total moles of lactonic sophorose lipids was 71%, and the mole percent of saturated fatty acid side chains based on the total moles of fatty acid side chains was 62%.

Figure 2:
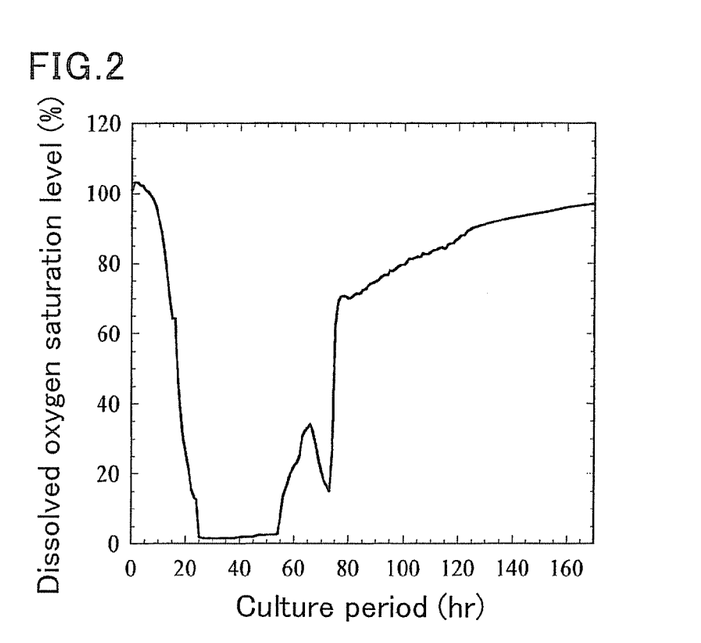
FIG. 2 is a graph showing a temporal change of the dissolved oxygen saturation level under an aeration condition of 0.5 vvm in Reference Example 1 of the present invention.

The temporal change of the dissolved oxygen saturation level during the culture process is illustrated in FIG. 2. The dissolved oxygen saturation level decreased to 2% one day after culture initiation and stayed at this level until the second day of the culture period. After the second day, the dissolved oxygen saturation level rose and never decreased to a level below 15% until the fourth day, that is, the end of the culture period.

Comparative Example 1

The same procedures as described in Example 2 were performed on the culture obtained in Reference Example 1. As a result, an oily substance (about 300 g) was obtained. Subsequently, the procedure for obtaining crystals was also performed on this oily substance but failed to yield any crystals at all. Thus, it was impossible to obtain sophorose lipids in a solid form.

Example 5

The same culture procedures as described in Example 1 were performed, except that palm oil was used as an oil for the main culture instead of Esterpal-M. The resulting culture was heated to 80° C., whereby sophorose lipids derived from palm oil (about 300 g) were precipitated in an oil form. This sophorose lipid oil was analyzed under the HPLC conditions described in Example 1. The results revealed that the mole percent of lactonic sophorose lipids was 97%, that the mole percent of the diacetyl lactone form based on the total moles of lactonic sophorose lipids was 83%, and that the mole percent of saturated fatty acid side chains based on the total moles of fatty acid side chains was 43%.

Example 6

The same procedures as described in Example 2 were performed on the sophorose lipid oil obtained in Example 5, whereby crystals were recovered. Thus, solid sophorose lipids (20 g) were obtained. The sophorose lipids were analyzed under the HPLC conditions described in Example 1. The results revealed that the mole percent of lactonic sophorose lipids was 100%, that the mole percent of the diacetyl lactone form based on the total moles of lactonic sophorose lipids was 95%, and that the mole percent of saturated fatty acid side chains based on the total moles of fatty acid side chains was 80%.

Example 7

The antibacterial and antifungal activities were analyzed for the sophorose lipids obtained in Examples 1, 2 and 5. An amount of 5 ml of a liquid medium (1% meat extract, 1% polypeptone, 0.5% yeast extract and 0.3% sodium chloride, pH 7.0) was dispensed to a test tube ($\phi$ 24 mm) and sterilized by steam at 121° C. for 20 minutes. One platinum loop of the bacterial or yeast strain shown in Table 1 was inoculated to the liquid medium and cultured with shaking at 30° C. for 24 hours. Thus, a seed culture was prepared. Each sample of the sophorose lipids was added to the same medium to a concentration of 0.001 to 0.1%, and then 50 μl of the seed culture was inoculated thereto. The mixture was cultured with shaking at 30° C. for 15 hours. The resulting culture was 41-fold diluted with water and the absorbance at 550 nm was measured. The absorbance measured in control experiments with no addition of sophorose lipids was taken as 100% and a relative value to this absorbance was calculated for each sample and was regarded as a growth degree. Table 1 shows the results. Among the examined sophorose lipids, those which have a higher mole percent of saturated fatty acid side chains strongly inhibited growth of the gram-positive bacteria and yeast at the lower concentrations.

TABLE 1

| Sample | | Growth degree (%)* Gram-positive bacteria | | | | | |
|---|---|---|---|---|---|---|---|
| | Mole percent of saturated fatty acid side chains | *Bacillus subtilis* ATCC 14593 Concentration of added sophorose lipids (%) | | | *Staphylococcus epidermidis* NBRC 3762 Concentration of added sophorose lipids (%) | | |
| Name | (%) | 0.1 | 0.01 | 0.001 | 0.1 | 0.01 | 0.001 |
| Solid sophorose lipids (Example 2) | 92 | — | 0 | 108 | — | 2 | 94 |
| Sophorose lipids (Example 1) | 75 | 0 | 77 | 101 | 1 | 49 | 99 |
| Sophorose lipids (Example 5) | 43 | 1 | 86 | — | 49 | 80 | — |
| Control (Sophorose lipid free) | — | 100 | 100 | 100 | 100 | 100 | 100 |

TABLE 1-continued

| | | Growth degree (%)* | | | | | |
|---|---|---|---|---|---|---|---|
| | | Gram-positive bacteria *Corynebacterium acetoacidophilum* ATCC 21478 Concentration of added sophorose lipids (%) | | | Gram-negative bacteria | | Yeast |
| Sample | | | | | *Escherichia coli* NBRC 3992 Concentration of added sophorose lipids (%) | *Pseudomonas putida* NBRC 3738 Concentration of added sophorose lipids (%) | *Saccharomyces cerevisiae* NBRC 0209 Concentration of added sophorose lipids (%) |
| Name | Mole percent of saturated fatty acid side chains (%) | 0.1 | 0.01 | 0.001 | 0.1 | 0.1 | 0.1 |
| Solid sophorose lipids (Example 2) | 92 | 2 | 1 | 51 | 84 | 88 | 25 |
| Sophorose lipids (Example 1) | 75 | 1 | 1 | 94 | 90 | 89 | 64 |
| Sophorose lipids (Example 5) | 43 | 1 | 6 | 101 | 90 | 92 | 103 |
| Control (Sophorose lipid free) | — | 100 | 100 | 100 | 100 | 100 | 100 |

*Growth degree (%): the growth (absorbance at 550 nm) of the control was taken as 100%, and the growth when each sample of the sophorose lipids was added to the medium was expressed as a relative value to the growth of the control.
The "—" means that no experiment was conducted.

Example 8

The antifungal activity was analyzed for the sophorose lipids obtained in Examples 1, 2 and 5. An amount of 8 ml of an agar medium (0.2% sodium nitrate, 0.1% dipotassium hydrogen phosphate, 0.05% potassium chloride, 0.05% magnesium sulfate heptahydrate, 0.001% iron sulfate heptahydrate, 3% sucrose and 1.5% agar) was prepared in a test tube (ϕ 18 mm) and sterilized by steam at 121° C. for 20 minutes. One platinum loop of the mold strain shown in the table below was inoculated to this agar medium and cultured at 30° C. for two weeks. Thus, a sporulated slant was prepared. To this slant was added 5 ml of a 0.1% Tween 80 aqueous solution to give a suspension. The suspension was filtered through gauze. Thus, a spore suspension was obtained. A medium containing 2% glucose and 1% yeast extract was dispensed to a test tube (ϕ 24 mm) and sterilized by steam at 121° C. for 20 minutes. Each sample of the sophorose lipids was added to this liquid medium to a concentration of 0.1%, and then a 50 µl aliquot of the spore suspension was inoculated thereto. The mixture was cultured with shaking at 30° C. for one week. Growth of the molds was visually evaluated. Experiments in which growth of the molds was observed were evaluated as "+"; and experiments in which growth of the molds was not observed were evaluated as "−". Table 2 shows the results. Among the examined sophorose lipids, those which have a higher mole percent of saturated fatty acid side chains based on the total moles of fatty acid side chains more strongly inhibited growth of the molds.

TABLE 2

| Sample | | Test molds, Growth test* | |
|---|---|---|---|
| Name | Mole percent of saturated fatty acid side chains (%) | *Gloeophyllum striatum* NBRC 6429 | *Schizophyllum commune* NBRC 6503 |
| Solid sophorose lipids (Example 2) | 92 | − | − |
| Sophorose lipids (Example 1) | 75 | − | − |
| Sophorose lipids (Example 5) | 43 | + | − |
| Control (Sophorose lipid free) | — | + | + |

*+: Growth was observed
−: Growth was not observed

Example 9

The antifungal activity was analyzed for the sophorose lipids obtained in Examples 1, 2 and 5. An agar medium plate was prepared by adding each sample of the sophorose lipids at a concentration of 0.1% to a potato dextrose agar medium (NISSUI PHARMACEUTICAL Co., Ltd.), and then a piece of filter paper (ϕ 8 mm) was mounted on the plate. A spore suspension of the mold strain shown in the table below was prepared in the same manner as in Example 8, and a 5 µl aliquot of the spore suspension was inoculated to the filter paper and cultured at 30° C. for three days. Growth of the molds was visually evaluated and the diameter of grown mold colonies was measured. The growth degree was calculated by the following equation.

Growth degree(%)=(growth area diameter in experiment with addition of sophorose lipids)/(growth area diameter in control experiment with no addition of sophorose lipids)×100(%)

The results are summarized in Table 3. Among the examined sophorose lipids, those which have a higher mole percent of saturated fatty acid side chains based on the total moles of fatty acid side chains more strongly inhibited growth of the molds.

TABLE 3

| Sample | | Test molds, Growth degree (%)* | | | |
|---|---|---|---|---|---|
| Name | Mole percent of saturated fatty acid side chains (%) | Aspergillus niger NBRC 4091 | Cladosporium resinae NBRC 8588 | Fusarium oxysporum NBRC 5942 | Penicillium claviforme NBRC 5739 |
| Solid sophorose lipids (Example 2) | 92 | 56 | 0 | 63 | 60 |
| Sophorose lipids (Example 1) | 75 | 61 | 0 | 75 | 66 |
| Sophorose lipids (Example 5) | 43 | 74 | 0 | 92 | 68 |
| Control (Sophorose lipid free) | — | 100 | 100 | 100 | 100 |

*Growth degree (%) = (growth area diameter in experiment with addition of sophorose lipids)/(growth area diameter in control experiment with no addition of sophorose lipids) × 100

Example 10

To 5 g of the solid sophorose lipids obtained in Example 2 was added 2.5 g of a 40% sodium hydroxide aqueous solution, and the mixture was stirred at room temperature for one hour. Subsequently, the pH of the mixture was adjusted to 7 with concentrated hydrochloric acid. The resulting mixture was analyzed under the HPLC conditions described in Example 1. The results revealed that lactonic sophorose lipids were not detected at all and all were converted into the acid form. Thus, by this method, a transparent, colorless, high-purity, high-content acidic sophorose lipid aqueous solution was obtained.

The invention claimed is:

1. A method for producing lactonic sophorose lipids, comprising
culturing a yeast of the genus *Candida* or *Torulopsis* in a culture medium containing a vegetable oil or fat, a fatty acid produced from a vegetable oil or fat, or a derivative thereof under limited oxygen supply,
wherein oxygen supply is controlled such that a dissolved oxygen saturation level is 20% or lower during the culturing, and
wherein the mole percent of diacetyl lactonic sophorose lipids is not lower than 80% based on the total moles of the lactonic sophorose lipids.

2. The production method according to claim 1, further comprising
crystallizing the lactonic sophorose lipids to separate the lactonic sophorose lipids in a solid form.

3. A method for producing acidic sophorose lipids, comprising
producing a lactonic sophorose lipids by culturing a yeast of the genus *Candida* or *Torulopsis* in a culture medium containing a vegetable oil or fat, a fatty acid produced from a vegetable oil or fat, or a derivative thereof under limited oxygen supply,
wherein oxygen supply is controlled such that a dissolved oxygen saturation level is 20% or lower during the culturing, and
wherein the mole percent of diacetyl lactonic sophorose lipids is not lower than 80% based on the total moles of the lactonic sophorose lipids, and
hydrolyzing the lactonic sophorose lipids.

4. A method for producing a surface active agent which comprises
using the lactonic sophorose lipids produced by the method according to claim 1, or
using the acidic sophorose lipids produced by the method according to claim 3.

5. A method for producing an antibacterial or antifungal agent which comprises
using the lactonic sophorose lipids produced by the method according to claim 1, or
using the acidic sophorose lipids produced by the method according to claim 3.

6. A method for producing a medicament which comprises
using the lactonic sophorose lipids produced by the method according to claim 1, or
using the acidic sophorose lipids produced by the method according to claim 3.

* * * * *